United States Patent [19]
Brunken

[11] Patent Number: 5,529,175
[45] Date of Patent: Jun. 25, 1996

[54] PACKAGE WITH SURGICAL SUTURE MATERIAL

[75] Inventor: Dieter Brunken, Huttblek, Germany

[73] Assignee: Ethicon, Inc., Somerville, N.J.

[21] Appl. No.: 322,256

[22] Filed: Oct. 13, 1994

[30] Foreign Application Priority Data

Oct. 15, 1993 [DE] Germany .......................... 43 35 659.1

[51] Int. Cl.$^6$ .................................... A61B 17/06
[52] U.S. Cl. ........................................... 206/63.3
[58] Field of Search .................. 206/63.6, 227, 206/380, 388, 63.3

[56] References Cited

U.S. PATENT DOCUMENTS

| | | | |
|---|---|---|---|
| 3,444,994 | 5/1969 | Kaepernik et al. | 206/63.3 |
| 4,700,833 | 10/1987 | Smith | 206/63.3 |
| 5,101,968 | 4/1992 | Henderson et al. | 206/227 |
| 5,390,782 | 2/1995 | Sinn | 206/63.3 |
| 5,425,445 | 6/1995 | Brown et al. | 206/63.3 |

*Primary Examiner*—Thomas P. Hilliard
*Attorney, Agent, or Firm*—Emil Richard Skula

[57] ABSTRACT

A package with surgical suture material consists of a base plate (1), a cover plate (30) and a closure plate (50). The thread (20) of a needle/thread combination is placed on the base plate (1) in several coils (24), whereby it travels through a thread guide (10, 12) and whereby in the lower region of the base plate (1) the individual coils are laid spaced apart, so that the innermost coil (25) is the one nearest to the front end (21) of the thread. The needle (22) is held by a needle holder (26). Arranged in the lower region of the cover plate (30) are brake strips (32, 33) which press against the lower regions at least of the outer coils (24) of the thread (20) when the cover plate (30) is folded onto the base plate (1). In the finished folded-together state the closure plate (50) covers the cover plate (30).

11 Claims, 4 Drawing Sheets

PACKAGE WITH SURGICAL SUTURE MATERIAL

The invention relates to a package with surgical suture material.

BACKGROUND OF THE INVENTION

Surgical suture material is used in the form of threads provided with needles, i.e. needle/thread combinations, and optionally also in the form of individual threads in pre-cut lengths. Various types of material are available for the threads, such as for example silk, polyamides, polypropylene or interwoven polyester and resorbable materials, in various thread thicknesses and thread lengths. As needles, a number of different straight and bent needles are used, which differ in needle size, needle thickness and type of section.

The package of surgical suture material has to guarantee that the contents remain safe and sterile. Usually, a sterile inner package is enclosed by an outer cover which keeps the inner package sterile until it is torn open and removed during an operation. The inner package, which is designated in the following as "package", should allow the surgical suture material to be removed rapidly and without complication. In particular, the thread to be removed should not become entangled or entwined, and moreover, it is to be ensured that the thread, after its removal, does not have a tendency to resume the shape which it assumed whilst in the package ("thread memory").

There are packages for a needle/thread combination which satisfy these requirements by keeping the thread in an extruded plastic channel. Kinks in the thread which promote the thread memory effect are thus avoided. To remove, the thread is pulled out from the plastic channel.

It is a disadvantage with the previously known package that it is costly as a result of the expensive channel. It also does not follow the trend of avoiding plastic waste.

SUMMARY OF THE INVENTION

It is the object of the invention to provide a package with surgical suture material, which can be manufactured inexpensively, does not cause any unnecessary plastics waste and permits a simple and reliable removal of the contained needle/thread combination.

This object is achieved by a package with surgical suture material having the features of claim 1. Advantageous versions arise from the dependent claims.

The package with surgical suture material has a base plate, to which is attached a thread guide in the proximity of one short side. The thread of a needle/thread combination having a needle attached to the front end of the thread is placed in several coils on the upper side of the base plate. It travels through the thread guide, whilst in the area of the base plate opposite the thread guide the individual coils are spaced apart such that the innermost coil is the one nearest to the front end of the thread. The needle is held by a needle holder. A part of the base plate is covered by a cover plate to which is attached at least one brake strip which presses at least against the outer coils of the thread. A closure plate, which conceals the cover plate at least partially and allows the removal of the needle with the thread attached to it, serves as the uppermost layer.

As a result of the fact that, in one partial area of the base plate, the individual coils of the thread are arranged in a spaced apart manner and, in this area, are pressed against the base plate by the brake strip attached to the cover plate, the thread cannot become entwined when it is being removed from the package. When the operator grips the needle with a needle holder and pulls on it, the innermost coil of the thread comes out of the package first, then the next one and finally the outermost coil. The at least one brake strip prevents the thread coils from slipping and running into one another in the area where they are placed spaced apart, something which would lead to problems on removing the thread. It has been shown that, to avoid the threads becoming entwined, it is sufficient if the coils in a partial region of the base plate lie spaced apart. The package with surgical suture material is therefore constructed in a space-saving manner, and during manufacture the thread can be coiled easily. Narrow bend radii or even kinks do not occur, meaning that the thread memory effect is reliably avoided. Since no channel is provided for the thread, no large forces of friction or even blockages occur on removal.

The thread guide is preferably formed of a first flap, which can be folded over from the short side of the base plate onto the upper side of the base plate, and a guide member which is arranged as a ramp, cut out from the base plate, which is raisable about a fold line. The ramp, whose free edge adjoins the closure plate, also prevents the needle from becoming entwined in the thread coils in the area of the thread guide on removing the needle/thread combination.

Preferably two brake strips are provided which are formed in one piece with the cover plate and which are foldable onto the cover plate along fold lines facing one another in the shape of a V.

In an advantageous version, a strip which presses against the base plate when the cover plate is folded over is arranged at the side of the cover plate opposite the brake strips. The strip prevents the thread coils from being pulled too far inwards when removing the needle/thread combination.

A piece of foam, provided with a slit for the needle and glued onto the upper side of the base plate, preferably serves as the needle holder. Silicone foam is for example suitable for this.

The needle holder can also be attached by a method other than gluing. The slit is preferably cut to correspond to the shape of the needle. This simplifies the removal of the needle and the gripping position is always the same. Since the needle is not inserted into the piece of foam with its tip, the tip cannot be damaged. The needle holder can also be designed to hold two needles, the second needle being attached to the rear end of the thread.

In a preferred version, the closure plate extends over the full length of the base plate and has, in the region of the needle holder, an aperture which permits the removal of the needle or needles. In this version the package does not need to be torn open. The needle with the thread attached to it can be removed easily through the aperture.

The package is designed as a folding package and can therefore be produced inexpensively. It consists—optionally except for the needle holder—of a uniform material, preferably cardboard.

The invention is described in more detail below with reference to an embodiment. The diagrams show:

DETAILED DESCRIPTION OF THE PREFERRED EMBODIMENTS

Figure 1:
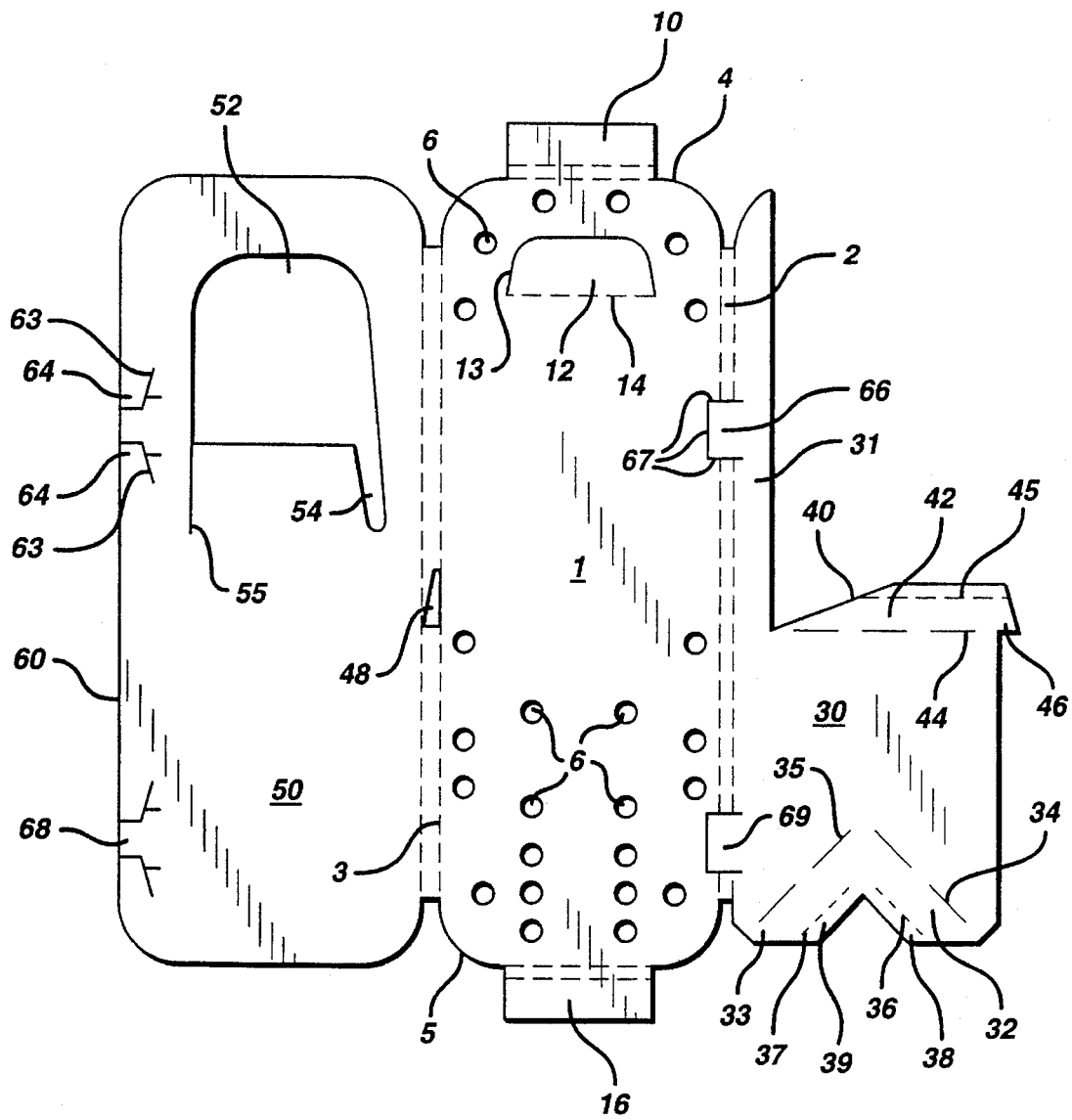
FIG. 1 a top view of a cut-out for an embodiment of the package, the base plate being viewed from underneath, FIG. 2 a perspective view of the package from FIG. 1, whereby the base plate is visible from the upper side, some parts are pre-folded and a needle/thread combination is on the base plate, FIG. 3 a perspective view of the package from FIG. 2, whereby the cover plate is folded over onto the base plate, and FIG. 4 a perspective view of the package from FIG. 2, whereby the closure plate is folded over onto the cover plate.

FIG. 1 shows the cut-out for an embodiment of the package. The cut-out preferably consists of cardboard. The material is cut through completely at the unbroken lines, whilst fold lines are represented by the dashed lines.

Figure 2:
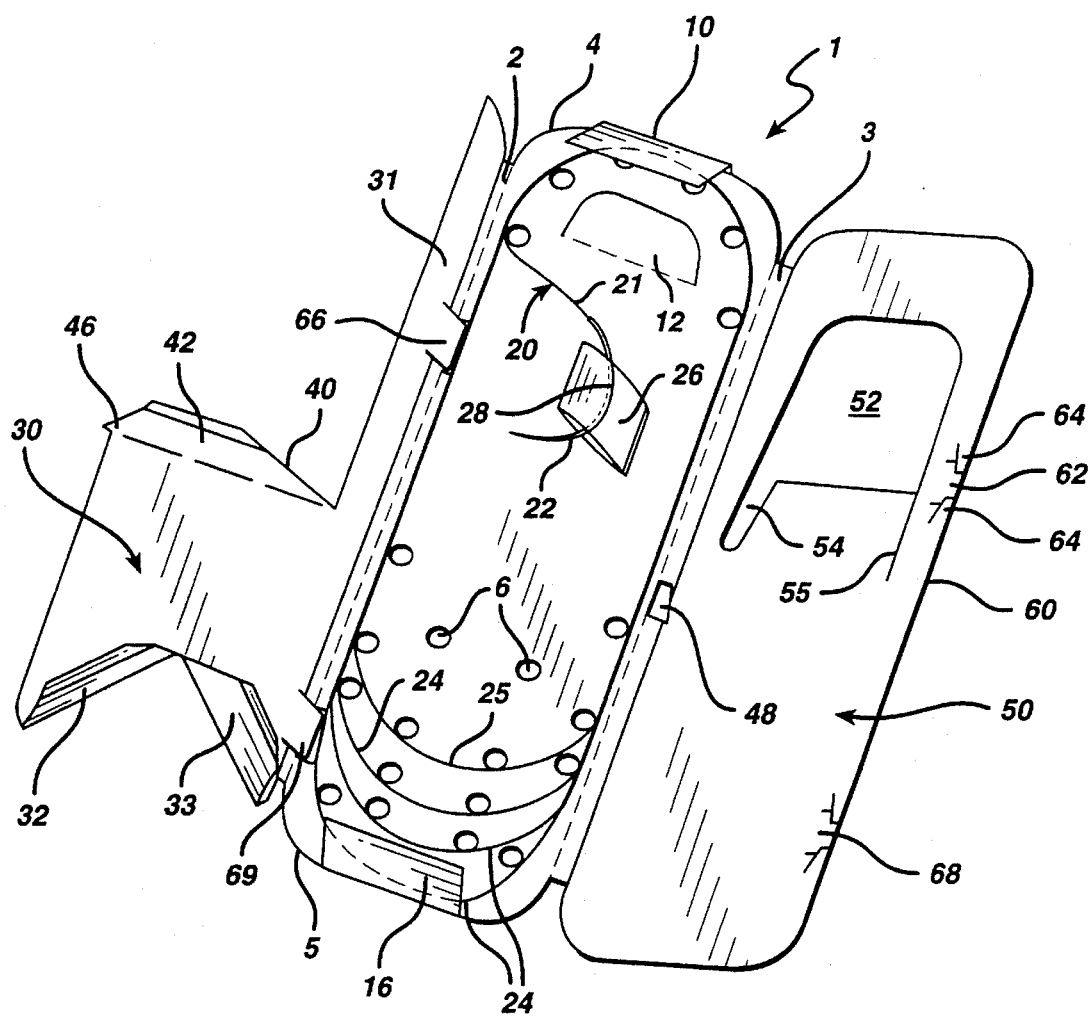

The best overview of the package with surgical suture material is given in FIG. 2 which shows the situation after the needle/thread combination has been coiled up and some parts have been pre-folded, but before the package is finally folded together.

A base plate 1 has an essentially rectangular basic shape with a first long side 2, a second long side 3, a top short side 4 and a bottom short side 5. Holes 6 through which pins are inserted for coiling up the thread, as described below, are punched in the base plate 1.

A first flap 10, which is folded onto the base plate 1, is joined to the top short side 4 of the base plate 1 along two fold lines. The first flap 10 serves, together with a ramp 12, as a thread guide. The ramp 12 is formed from the base plate 1 by means of a cut line 13 which essentially extends over three sides of a rectangle, and is folded upwards along a fold line 14 which is the fourth side of the rectangle. The first flap 10 prevents the suture material from coming out of the package at the top short side 4. The ramp 12 ensures that it cannot slip too far into the central area of the package. A second flap 16, corresponding in shape and action to the first flap 10, is formed at the bottom short side 5 of the base plate 1.

The surgical suture material consists of a thread 20 and a needle 22 which is attached to the front end 21 of the thread. The thread 20 lies on the base plate 1 in several coils 24. In the lower region of the base plate 1, the coils 24 lie spaced apart. The innermost coil 25 is the one nearest to the front end 21 of the thread, whilst the outermost coil forms the end of the thread 20. The needle 22 is held by a needle holder 26, which consists of a piece of foam, preferably silicone. The needle holder 26 is provided with a slit 28 which is matched to the shape of the needle and into which the needle 22 is pushed. The needle holder 26 is glued onto the upper side of the base plate 1.

In the production of the package, pins are pushed through some of the holes 6 to coil up the thread, in order to define the outline of a coil 24 of the thread 20. The pins remain inserted in the (in the embodiment example six) holes in the proximity of the top short side 4 of the base plate 1 throughout the entire coiling process. After the needle 22 has been pushed into the needle holder 26, the innermost coil 25 is laid first, pins through the four holes in the lower region of the innermost coil 25 serving as a means of aid. These pins are then pulled out whilst four other pins are inserted through the four holes underneath which define the outline in the lower region of the next innermost coil. After this coiling has been carried out, these pins are also pulled out, etc. Finally, the outermost of the coils 24 is coiled. In FIG. 2, four further holes 6 are visible within the innermost coiling 25 which are only used if a longer thread is used, the innermost coil of which lies even further inside than the innermost coil 25 of the embodiment.

Figure 3:
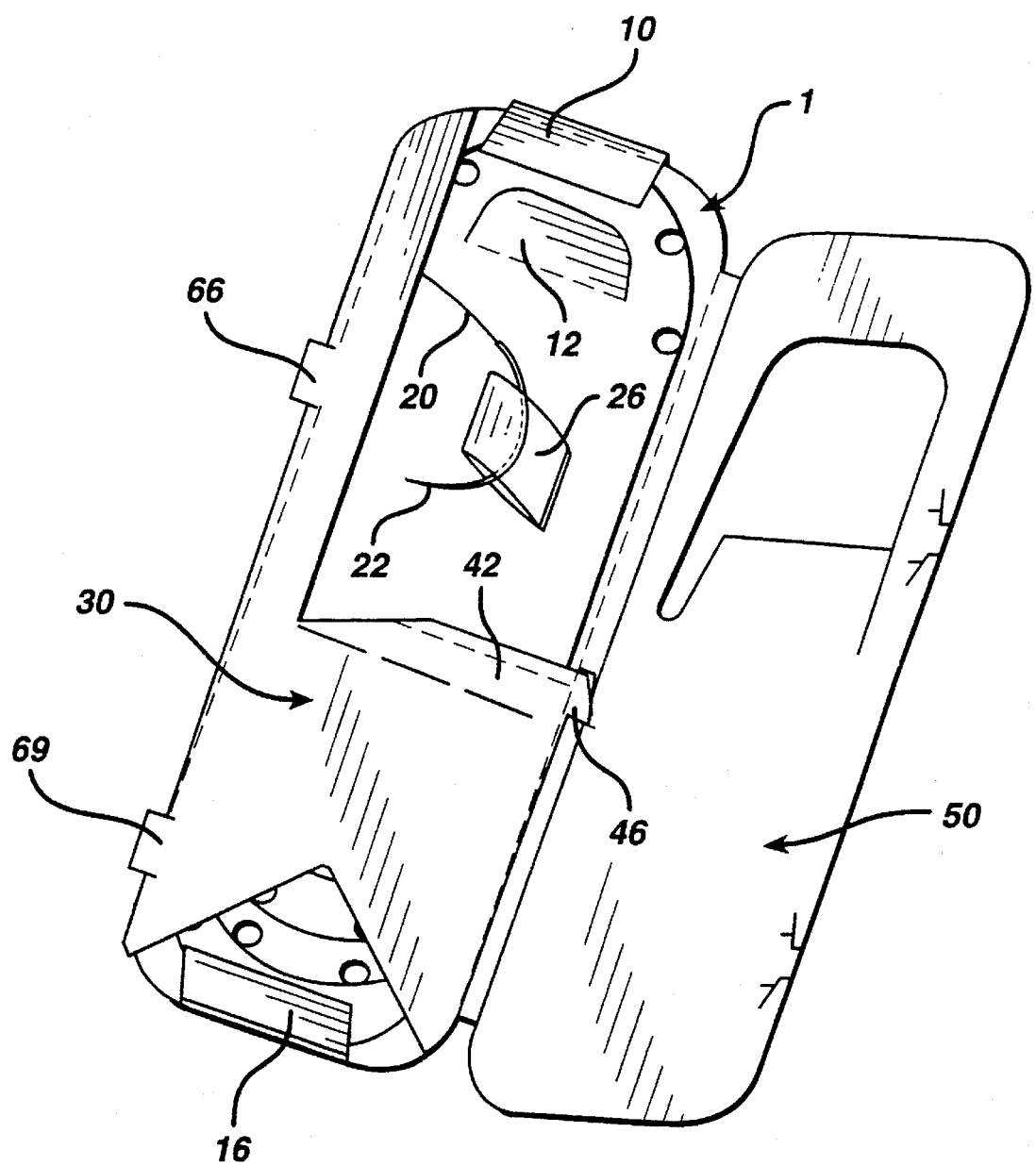

The base plate 1 is joined at its first long side 2 to a cover plate 30 via two fold lines running parallel to each other. The cover plate 30, if it is folded onto the base plate 1 (see FIG. 3), essentially covers the lower region of the base plate 1. However, in the embodiment, the cover plate 30 also has another strip 31 which extends up to the top short side 4 of the base plate 1. A first brake strip 32 and a second brake strip 33 are formed at the bottom side of the cover plate 30. The first brake strip 32 is folded onto the cover plate 30 along a fold line 34, whilst the second brake strip 33 is bent around a fold line 35. The two fold lines 34 and 35 face each other in the shape of a V. Provided at the first brake strip 32 is another fold line 36, around which an end region 38 of the first brake strip can be slightly angled, onto the cover plate 30. Another fold line 37 and an end region 39 are correspondingly provided at the second brake strip 33. If the cover plate 30 is folded onto the base plate 1, as shown in FIG. 3, the first brake strip 32 and the second brake strip 33 press against the lower regions of the coils 24 of the thread 20, at least in the case of the outer coils 24. It is thus guaranteed that the lower regions of the coils of the section of thread still not removed do not slip whilst the needle/thread combination is removed, thus avoiding thread entanglement.

A strip 42 which is slightly angled along a fold line 44 onto the cover plate 30 is formed at the upper side 40 of the cover plate 30. The outer region of the strip 42 is angled along another fold line 45 in the other direction, so that it runs essentially parallel to the cover plate 30. A projection 46 at the strip 42 locks in an opening 48 situated at the second long side 3 if the cover plate 30 is folded over onto the base plate 1, see FIG. 3. The cover plate 30 is thereby secured in this position. The strip 42 prevents the thread coils from slipping too far upwards on removing the needle/thread combination.

Figure 4:
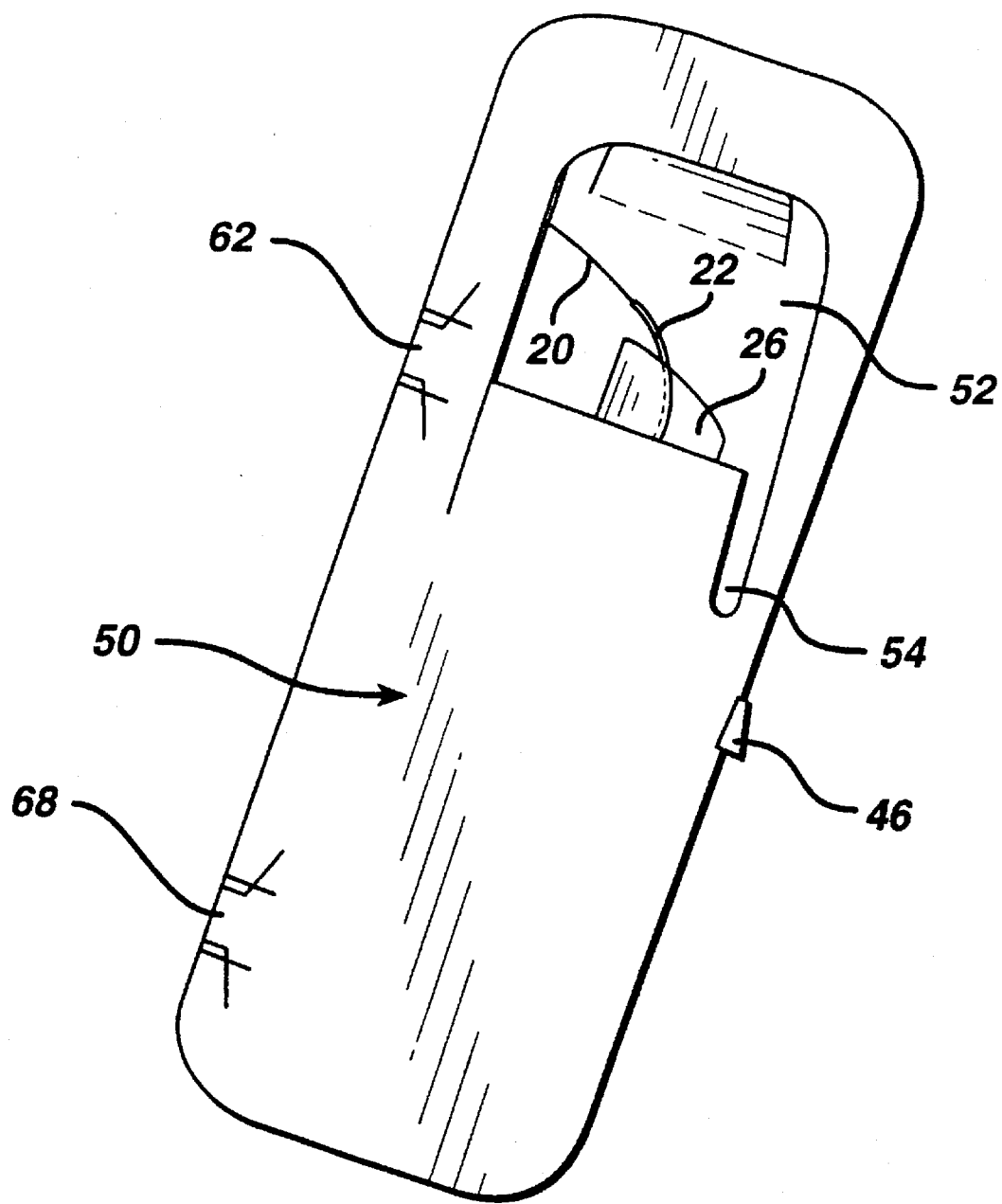

A closure plate 50 is joined to the second long side 3 of the base plate 1, along two parallel-running fold lines, the inside one of which coincides with the second long side 3 of the base plate 1. The closure plate 50 covers the largest part of the base plate 1 when it is folded over onto the cover plate 30, see FIG. 4. An aperture 52 is provided in the upper region of the closure plate 50. The aperture 52 allows access to the needle 22 without tearing open the package. The needle 22 can thus be grasped with a needle holder (gripper) in the proximity of the front end 21 of the thread and be pulled out from the needle holder 26. In the lower region of the aperture 52 there is a recess 54 and an incision 55 opposite it, so that the region of the closure plate 50 bordering the lower side of the aperture 52 can easily be raised if this should be necessary on removing the needle. On pulling out, the thread 20 glides through the recess 54, the rounded lower end region of which prevents damage to the thread 20.

For holding the package together, an upper closure strip 62 is provided on the free long side 60 of the closure plate 50, which strip is formed from several incisions 63, see FIG. 1. Two lugs 64, formed by the incisions 63, engage behind an upper counterpart 66 (see FIG. 3 and FIG. 4) and thus prevent the closure plate 50 from springing upwards. The upper counterpart 66 is formed by three incisions 67 extending over three sides of a rectangle, as shown in FIG. 1. On folding the cover plate 30 onto the base plate 1, the upper counterpart 66 swings outwards, as FIG. 2 and FIG. 3 show. A lower closure strip 68 which engages at a lower counterpart 69 is formed corresponding to the upper closure strip 62.

The package shown with surgical suture material is preferably in an outer package which is not shown. After sterilisation, for example by irradiation, the package shown remains sterile, even when the outer package is then exposed to the non-sterile surroundings. During an operation, the outer package is torn open by operation personnel working in non-sterile conditions, without touching the package shown. The latter can then be removed from the outer package by personnel operating in sterile conditions. The surgeon now has direct access to the needle 22, and the thread 20 attached thereto, via the aperture 52 and can remove the needle/thread combination, as described, from the package.

In an alternative version of the package, the closure plate is divided into two. In the folded-together state of the package, the lower part of the closure plate lies on the cover plate, whilst the upper part conceals the needle. In order to remove the needle/thread combination, the upper part of the closure plate must be folded away from the base plate.

I claim:

1. Package with surgical suture material, said package comprising a) a base plate (1) with a first long side (2), a second long side (3), a top short side (4) and a bottom short side (5), said base plate having a top surface and a bottom surface whereby there is a thread guide (10, 12) in the proximity of the top short side (4) and, arranged beneath the thread guide (10,12) on the top surface of the base plate (1), there is a needle holder (26), b) a needle/thread combination (20,22) with a needle (22) attached to a front end (21) of the thread, said thread comprising several individual coils whereby said coils (24) are laid on the top surface of the base plate (1), and travel through the thread guide (10, 12) and, in the region of the base plate (1) adjacent to the bottom side (5), the individual coils (24) are laid spaced apart, so that the innermost coil (25) is the one nearest to the front end (21) of the thread, and whereby the needle (22) is held by the needle holder (26), c) a cover plate (30) having a bottom which is connected to the base plate (1) and can be folded onto the top surface of the base plate (1), at least partially covering the base plate (1), whereby at least one brake strip (32,33) extends from the bottom of the cover plate (30), which strip is foldable onto the cover plate (30) and, when the cover plate (30) is folded over, presses against the outer coils (24) of the thread (20), and d) a closure plate (50) which is connected to the second long side (3) of the base plate (1) and is foldable onto the base plate (1), whereby the closure plate (50) at least partially conceals the cover plate (30) folded onto the top surface of the base plate (1).

2. Package with surgical suture material according to claim 1, characterized in that at the top short side (4) of the base plate (1) there is arranged a first flap (10), foldable onto the top surface of the base plate (1), which with a guide piece (12) arranged underneath forms the thread guide.

3. Package with surgical suture material according to claim 2, characterized in that the guide piece is a ramp (12) having a lower side, cut out of the base plate (1), which is raisable about a fold line (14) running along the lower side of the ramp (12).

4. Package with surgical suture material according to claim 1 characterized in that the cover plate (30) is connected to the first long side (2) of the base plate (1).

5. Package with surgical suture material according to claim 4, characterized in that a second flap (16) which can be folded onto the top surface of the base plate (1) is arranged at the bottom short side (5) of the base plate (1).

6. Package with surgical suture material according to claim 4 or 5, characterized in that two brake strips (32, 33) are provided which are formed in one piece with the cover plate (30) at the bottom side and which can be folded onto the cover plate (30) along fold lines (34, 35) facing each other in a manner of a letter V.

7. Package with surgical suture material according to claim 1 characterized in that at a top side (40) of the cover plate (30) there is formed a strip (42) which presses against the base plate (1) when the cover plate (30) is folded.

8. Package with surgical suture material according to claim 1 characterized in that the needle holder (26) comprises a piece of foam which is glued onto the top surface of the base plate (1) and provided with a slit (28) for the needle (22).

9. Package with surgical suture material according to claim 1 characterized in that a closure strip (62, 68), which engages at a counterpart (66, 69) along the first long side (2) of the base plate (1), is formed at a free long side (60) of the closure plate (50).

10. Package with surgical suture material according to claim 1 characterized in that the closure plate (50) extends over the entire length of the base plate (1) and has an upper aperture (52) which allows a needle (22) to be removed.

11. Package with surgical suture material according to claim 1 characterized in that the closure plate extends over the entire length of the base plate (1) and it divided into an upper part and a lower part, whereby the upper part can be folded away from the base plate in order to allow a needle to be removed.

* * * * *